(12) United States Patent
Mische et al.

(10) Patent No.: US 7,494,486 B2
(45) Date of Patent: Feb. 24, 2009

(54) METHOD OF REMOVING DEBRIS CORRESPONDING WITH THE R-WAVE

(76) Inventors: Hans Mische, 32 Highbanks Pl., St. Cloud, MN (US) 56301; Robert C. Beck, 2256 Hendon Ave., St. Paul, MN (US) 55108

( * ) Notice: Subject to any disclaimer, the term of this patent is extended or adjusted under 35 U.S.C. 154(b) by 0 days.

(21) Appl. No.: 10/952,469

(22) Filed: Sep. 28, 2004

(65) Prior Publication Data
US 2005/0124972 A1 Jun. 9, 2005

Related U.S. Application Data

(63) Continuation of application No. 10/231,507, filed on Aug. 30, 2002, now Pat. No. 6,800,075, and a continuation-in-part of application No. 10/145,699, filed on May 16, 2002, now Pat. No. 6,896,754, and a continuation-in-part of application No. 10/050,978, filed on Jan. 18, 2002, and a continuation-in-part of application No. 09/995,303, filed on Nov. 27, 2001, and a continuation-in-part of application No. 09/637,529, filed on Aug. 11, 2000, and a continuation-in-part of application No. 09/459,225, filed on Dec. 10, 1999, now abandoned.

(60) Provisional application No. 60/402,680, filed on Aug. 12, 2002, provisional application No. 60/316,122, filed on Aug. 30, 2001.

(51) Int. Cl.
*A61M 31/00* (2006.01)
*A61N 1/00* (2006.01)

(52) U.S. Cl. .................................. 604/509; 607/17

(58) Field of Classification Search ................. 604/503, 604/22, 506–509, 101.05, 96.01, 102.01, 604/187; 128/898; 607/17; 600/16–18
See application file for complete search history.

(56) References Cited

U.S. PATENT DOCUMENTS

| | | | | |
|---|---|---|---|---|
| 5,634,899 | A | * | 6/1997 | Shapland et al. ............. 604/507 |
| 6,605,074 | B2 | * | 8/2003 | Zadno-Azizi et al. ....... 604/509 |
| 2002/0091407 | A1 | * | 7/2002 | Zadno-Azizi et al. ....... 606/200 |
| 2004/0162488 | A1 | * | 8/2004 | Uber et al. ................... 600/432 |

* cited by examiner

*Primary Examiner*—Matthew F Desanto
(74) *Attorney, Agent, or Firm*—Beck + Tysver PLLC

(57) ABSTRACT

A method and device for injecting and extracting fluid at a treatment site to remove debris from the site.

3 Claims, 16 Drawing Sheets

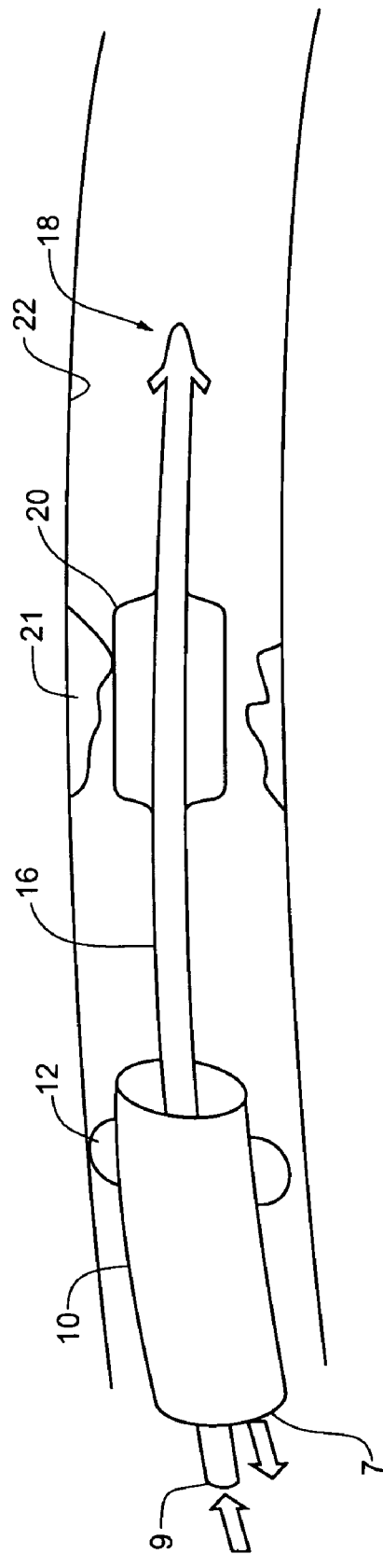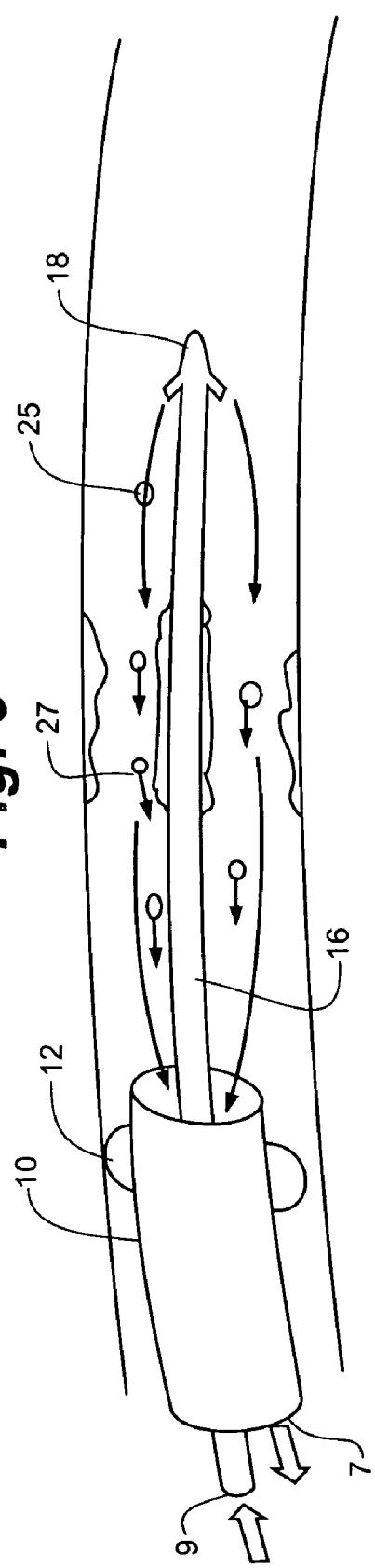

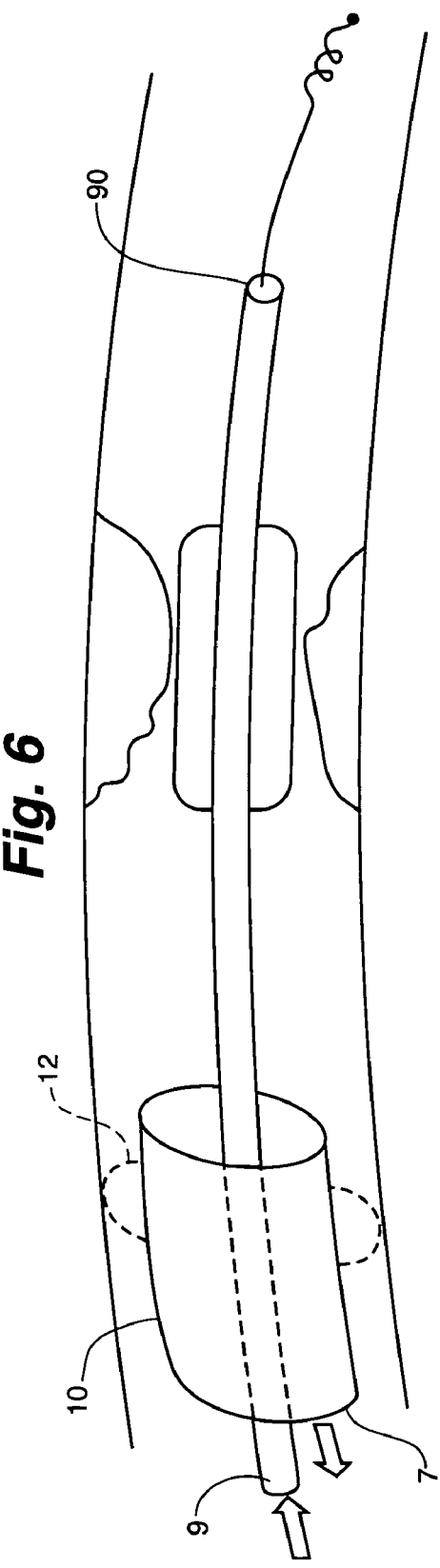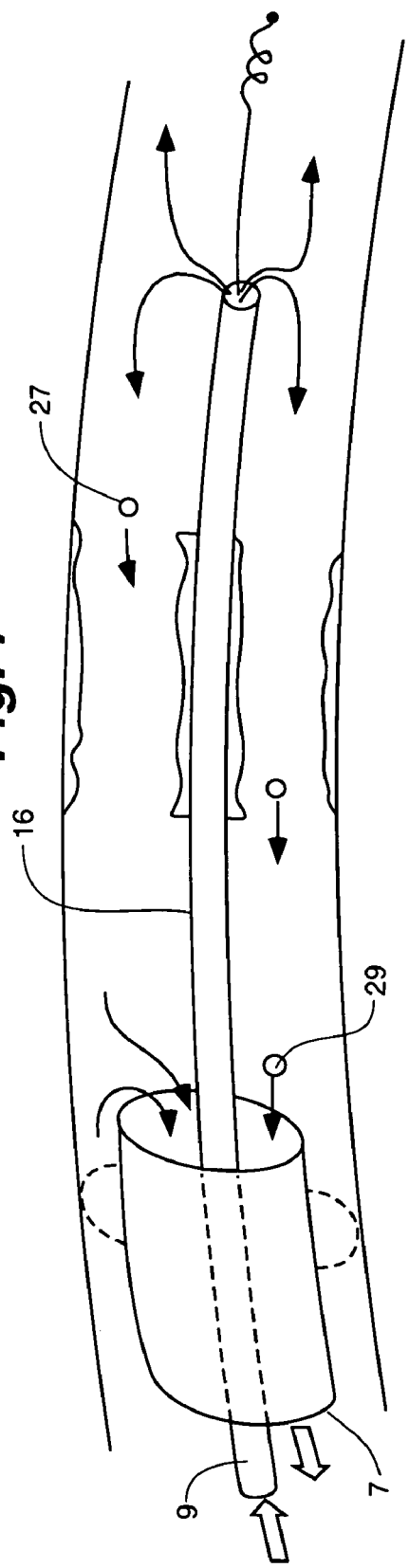

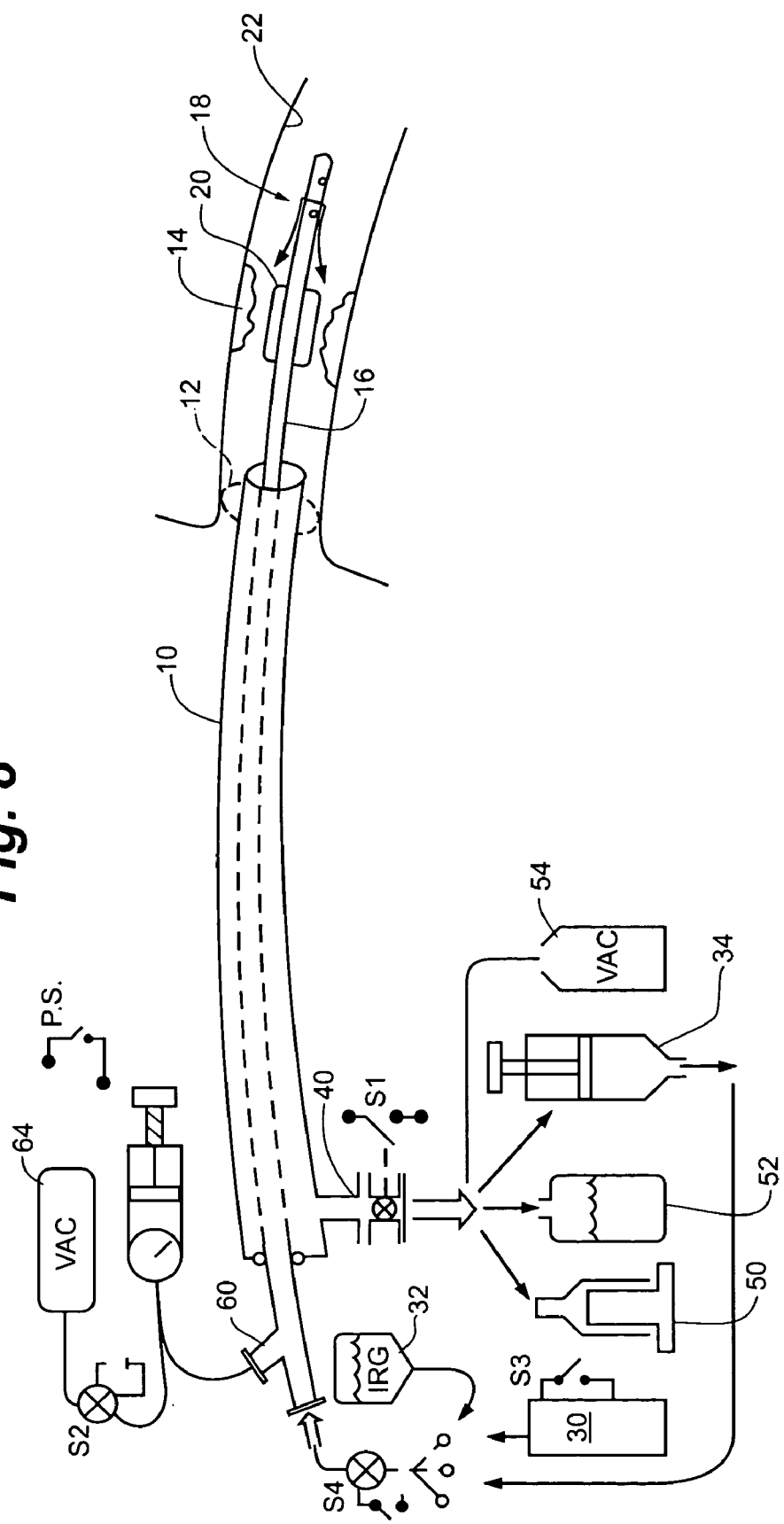

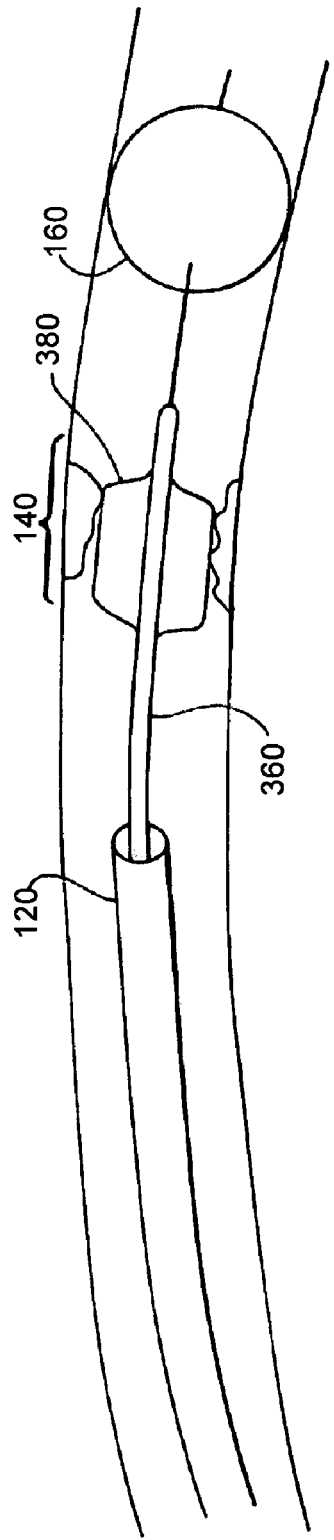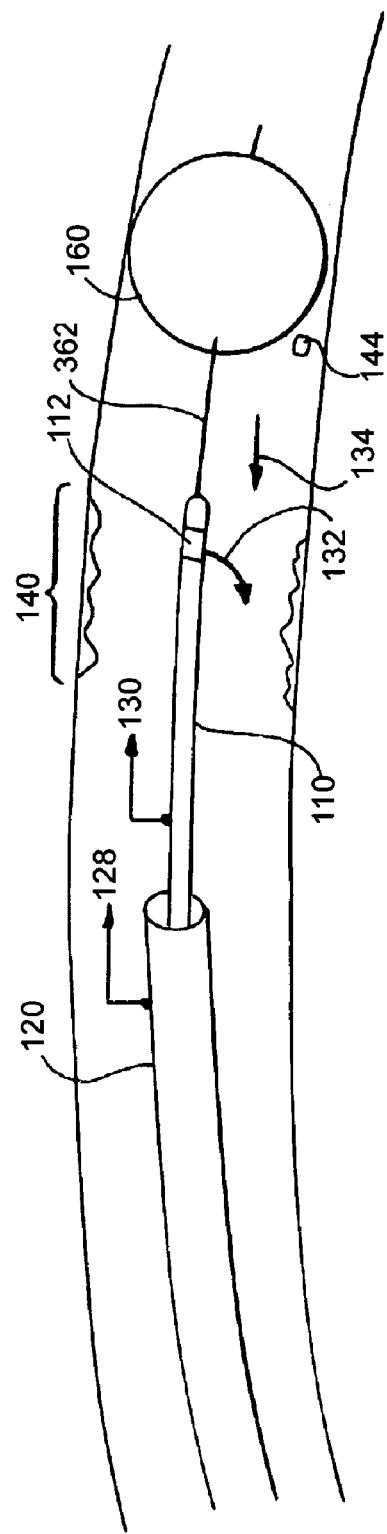

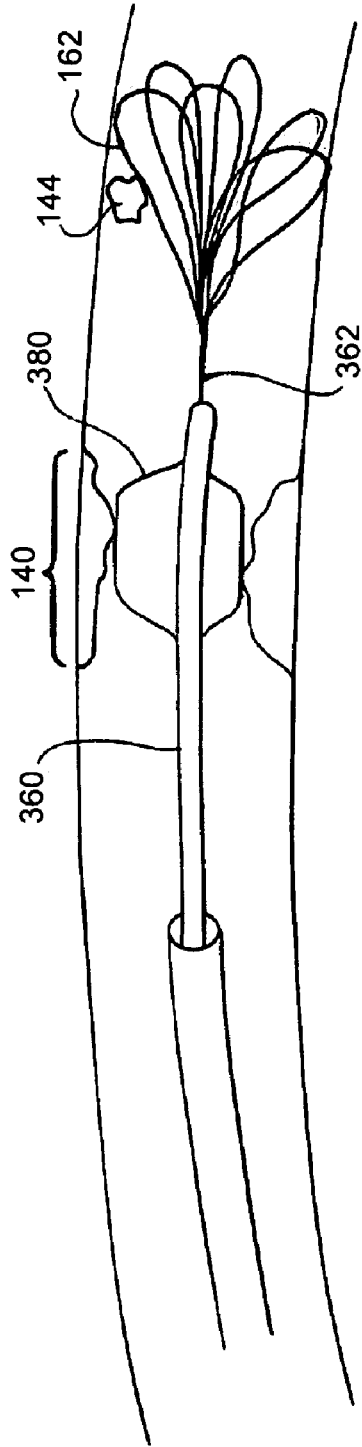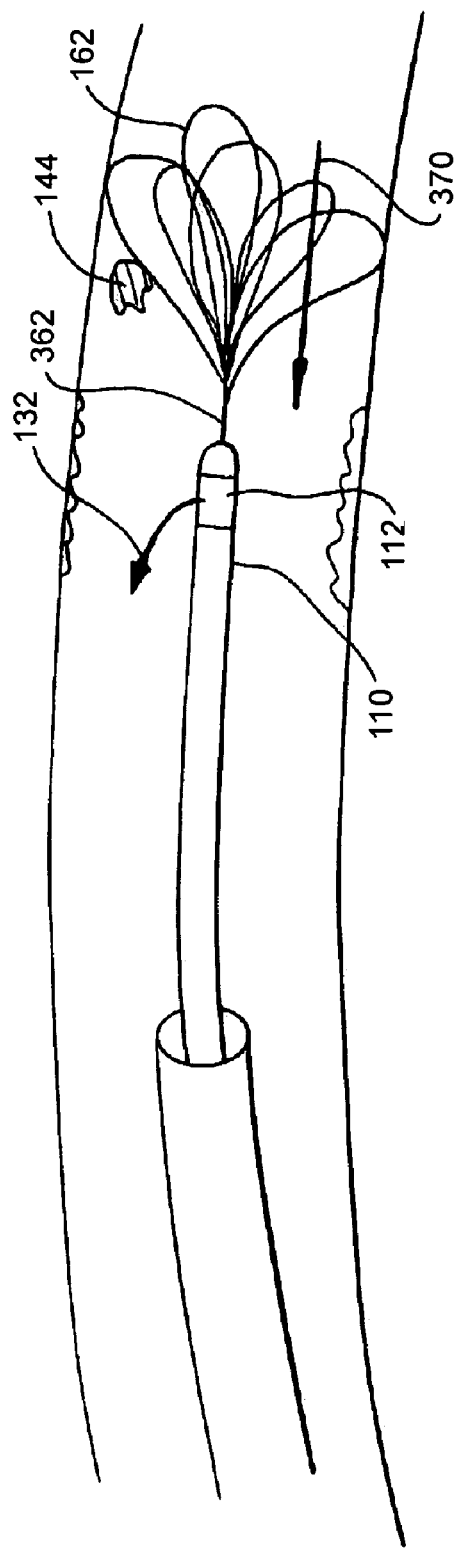

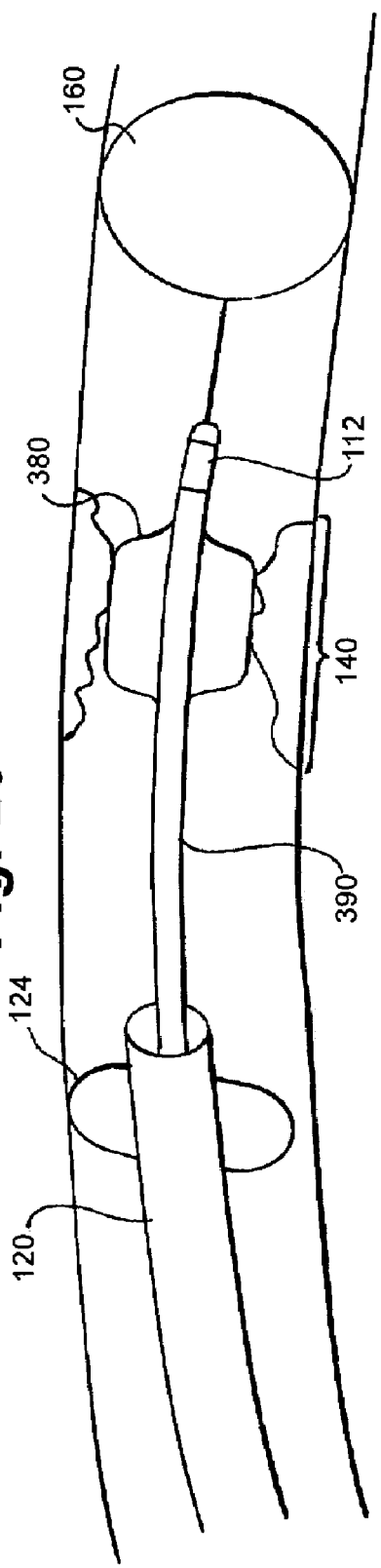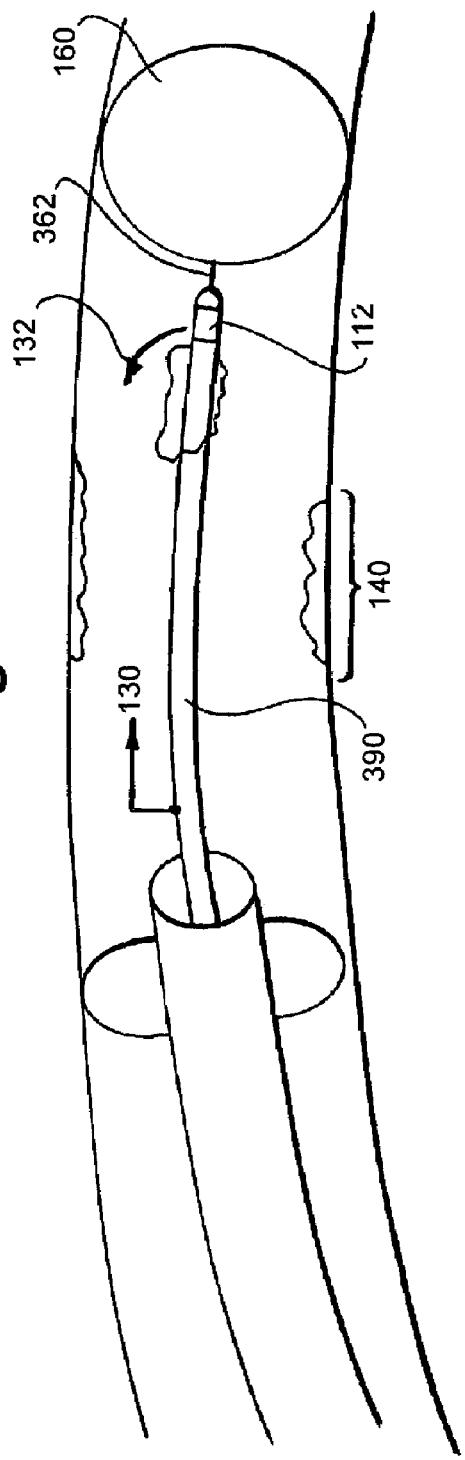

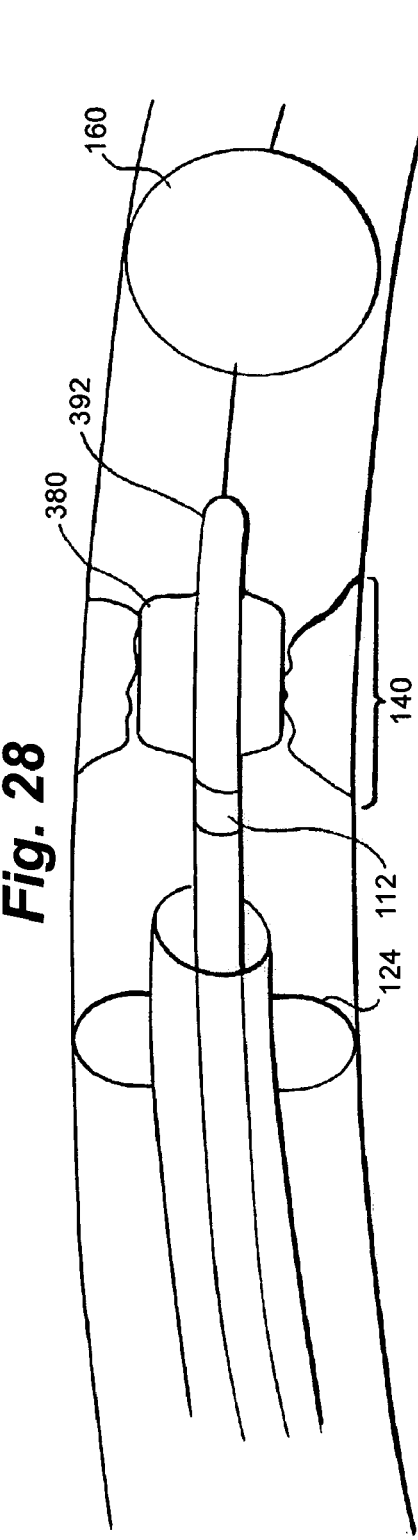
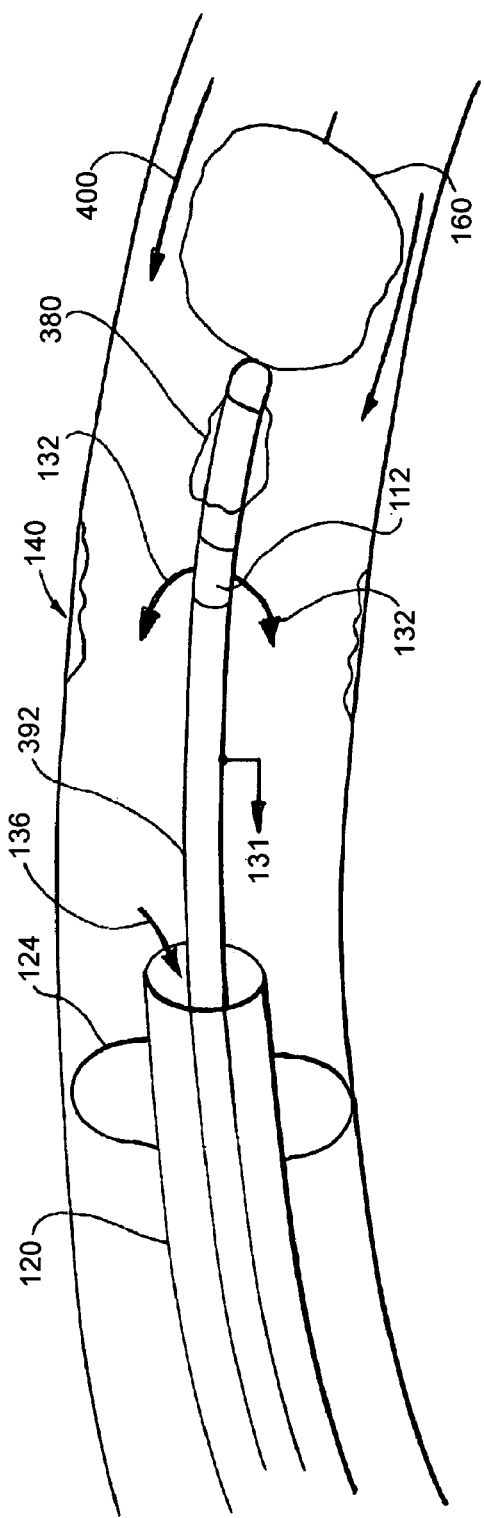

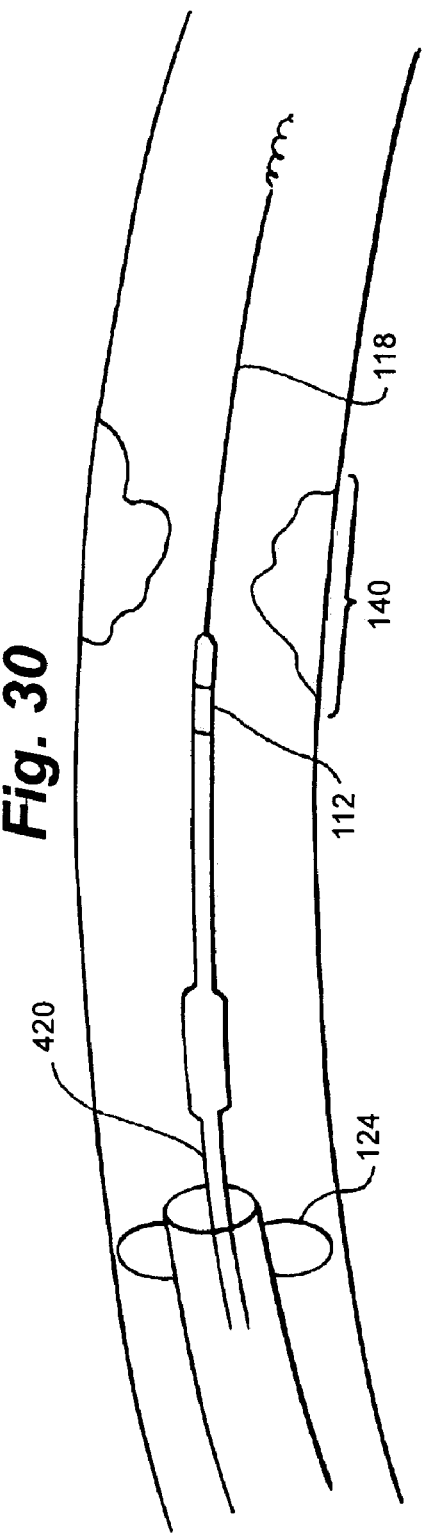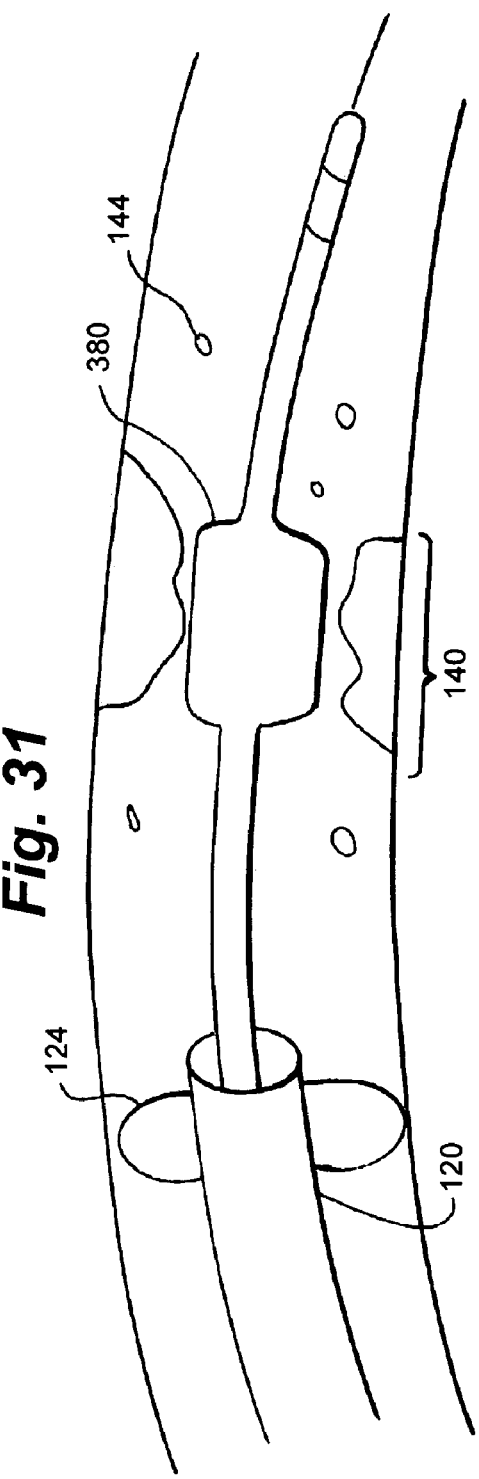

METHOD OF REMOVING DEBRIS CORRESPONDING WITH THE R-WAVE

CROSS REFERENCE

This application is a utility case based upon provisional applications U.S. 60/402,680 filed Aug. 12, 2002; U.S. 60/316,122 filed Aug. 30, 2001; and a continuation of U.S. Ser. No. 10/231,507 filed Aug. 30, 2002 (issued as U.S. Pat. No. 6,800,075), each is incorporated by reference herein in their entirety.

The application is a CIP of U.S. Ser. No. 09/637,529 filed Aug. 11, 2000; U.S. Ser. No. 09/459,225 filed Dec. 10, 1999 now abandoned; U.S. Ser. No. 09/995,303 filed Nov. 27, 2001; U.S. Ser. No. 10/050,978 filed Jan. 18, 2002; U.S. Ser. No. 10/145,699 filed May 16, 2002 now U.S. Pat. No. 6,896,754. Each is incorporated by reference herein in their entirety.

FIELD OF THE INVENTION

The present invention relates to cardiology and more particularly to devices and methods for removing debris from vessels.

BRIEF DESCRIPTION OF THE DRAWINGS

Throughout the figures like reference numerals indicate equivalent structure wherein:

FIG. 4 is a schematic of the invention;
FIG. 5 is a schematic of the invention;
FIG. 6 is a schematic of the invention;
FIG. 7 is a schematic of the invention;
FIG. 8 is a schematic of the invention;
FIG. 22 is a schematic showing a method of use;
FIG. 23 is a schematic showing a method of use;
FIG. 24 is a schematic showing a method of use;
FIG. 25 is a schematic showing a method of use;
FIG. 26 is a schematic showing a method of use;
FIG. 27 is a schematic showing a method of use;
FIG. 28 is a schematic showing a method of use;
FIG. 29 is a schematic showing a method of use.
FIG. 30 is a schematic showing a method of use;
FIG. 31 is a schematic showing a method of use; and,
FIG. 32 is a schematic showing a method of use.

DETAILED DESCRIPTION

Figure 1:
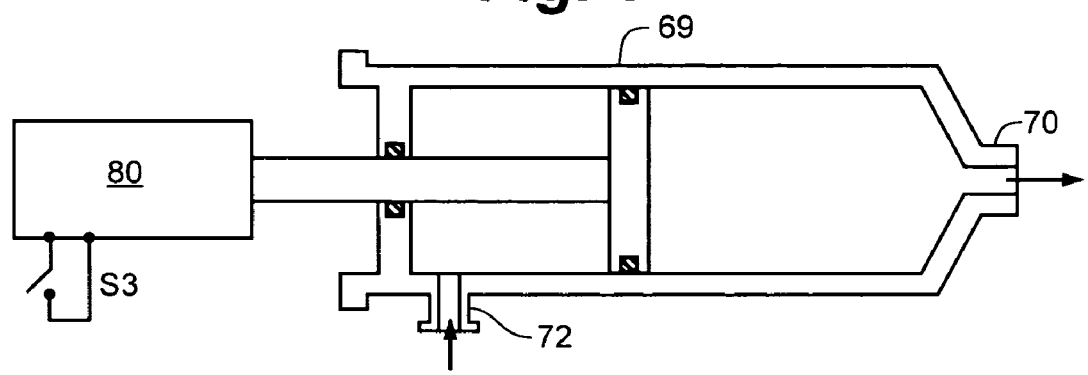
FIG. 1 is a schematic of the invention.

FIG. 8 shows the overall schematic of the treatment system. A guide sheath with an optional occlusion balloon 12 is navigated to the treatment site 14. A balloon catheter 16 with a distal fluid delivery port 18 or nozzle is passed trough the guide catheter 10 to the treatment site.

Fluid injected into the catheter 16 emerges from the catheter distal of the balloon 20 and induces a retrograde flow in the vessel 22.

The injected fluid may be saline, drugs or contrast agent or any biocompatible fluid. The source of fluid is selected from a conventional power injector 30 an irrigation bag suspended above the patient 32, a conventional syringe or a Gemini syringe 34.

The guide sheath is used to extract debris from the treatment site. The outflow passes trough a valve 40, which is associated with a switch S1. Preferably the valve 40 is actuated by closing S1 and/or the manual actuation of the valve sets the switch S1 to logic 1. The fluid drawn from the treatment site may be collected in a manual syringe 50 the low pressure side of Gemini 34 or a vacuum container 54 or a gravity fed collection bag 52.

The balloon inflation port 60 is coupled to inflation syringe 62 and a deflation vacuum reservoir 64 through a switch valve S2. Inflation of the balloon proceeds normally but deflation is preferably performed in synchrony with the heart. The physician activates the physician switch PS when he wants to deflate the balloon 20. Through logic, the valve S2 is opened and the balloon quickly deflated at an appropriate point in the cardiac cycle.

The catheter is freely movable within the sheath 10 both before during and after the procedure. That is the nozzle 18 can be "on" while the catheter is moving relative to the sheath.

FIG. 1 shows a Gemini dual syringe 69 with an injection outlet 70 and an extraction or recovery inlet 72. In this version of the device, it is attached to power injector 80, which maybe turned on, by the switch S3. The plunger 74 sweeps out a volume and the displaced fluid is injected out of the port 70. Recovered fluid from the sheath is collected at port 72. In this fashion the volume injected and extracted are directly coupled.

Figure 2:
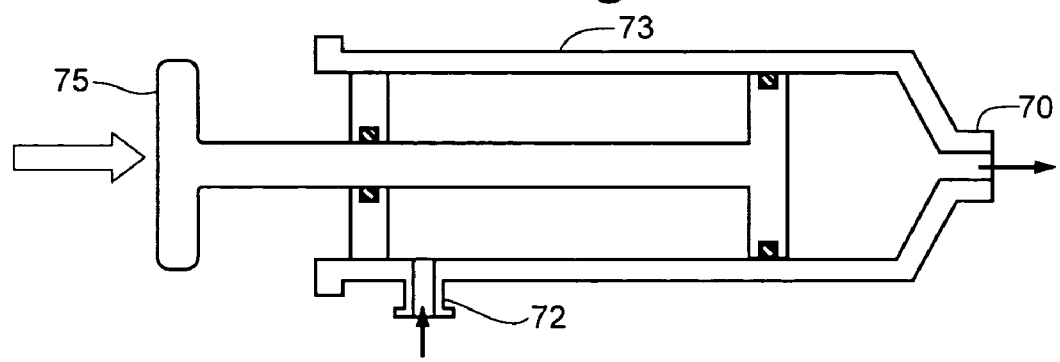
FIG. 2 is a schematic of the invention.

FIG. 2 shows a manually operated Gemini dual syringe 73 with a hand plunger 75. This version is useful for interventions where manual control of injection is desired.

Figure 3:
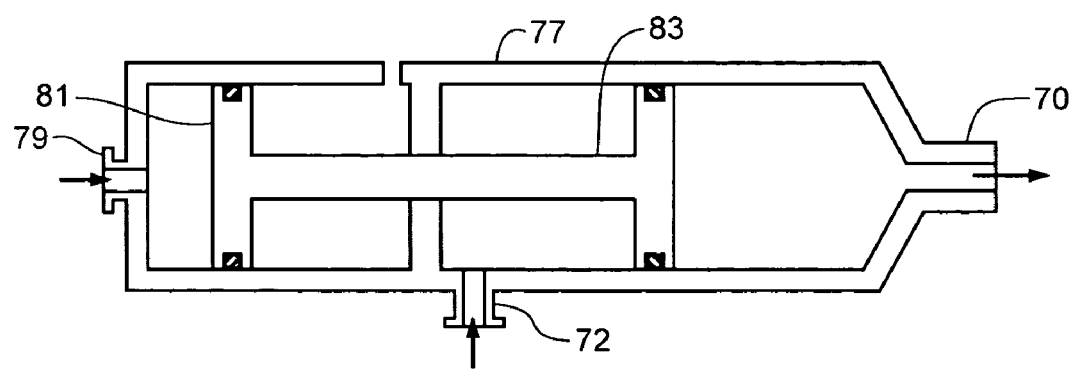
FIG. 3 is a schematic of the invention.

FIG. 3 shows a "universal" Gemini dual syringe 77 where an additional injection ports 79 and power piston 81 drive a plunger 83. The power inlet port 79 may couple to pump or power injector to control injection.

FIG. 4 and FIG. 5 should be considered together as depicting a method of removing debris from a vessel. In FIG. 4, the balloon is inflated to treat the lesion 21 in vessel 22. A fluid injection lumen 9 in the catheter terminates in a retrograde flow-inducing nozzle 18. At the conclusion of the intervention, the balloon is quickly deflated while fluid is injected with nozzle 18. The retrograde flow depicted by arrow 25 sweeps debris indicated by particle 27 into the open mouth of the guide catheter 10. It is preferred to synchronize the balloon deflation with the fluid injection at a time when the flow in the guide catheter is at a maximum and coronary flow is at a minimum. This flow in the sheath 10 out the lumen 7 is propelled by either the low pressure side of a Gemini syringe 72 or a manual syringe or a vacuum container 54 or a gravity fed bag relying on aortic pressure to force flow in the sheath 10 lumen.

In the method of FIG. 4 and FIG. 5 The occlusion of the vessel 22 with an occlusion balloon 12 is optional and used if the flow in the guide sheath lumen 7 is too low to collect all the injected fluid and debris.

FIG. 6 an FIG. 7 show an alternate debris collection concept where fluid is injected through a guide wire lumen 90 without attempting to induce a retrograde flow. It should be appreciated that a dedicated fluid injection lumen may be used as an alternative. In FIG. 6 an intervention takes place normally and in FIG. 7 a large amount of fluid is injected into the vessel distal of the lesion to displace debris toward the open mouth of the guide sheath 10. Particles such as 27 and particle 29 are forced into the guide sheath where they are evacuated. If the flow rate of the guide sheath exceeds the injected fluid flow rate then the debris will all be sucked out without the use of an optional occlusion balloon 12.

Figure 12:
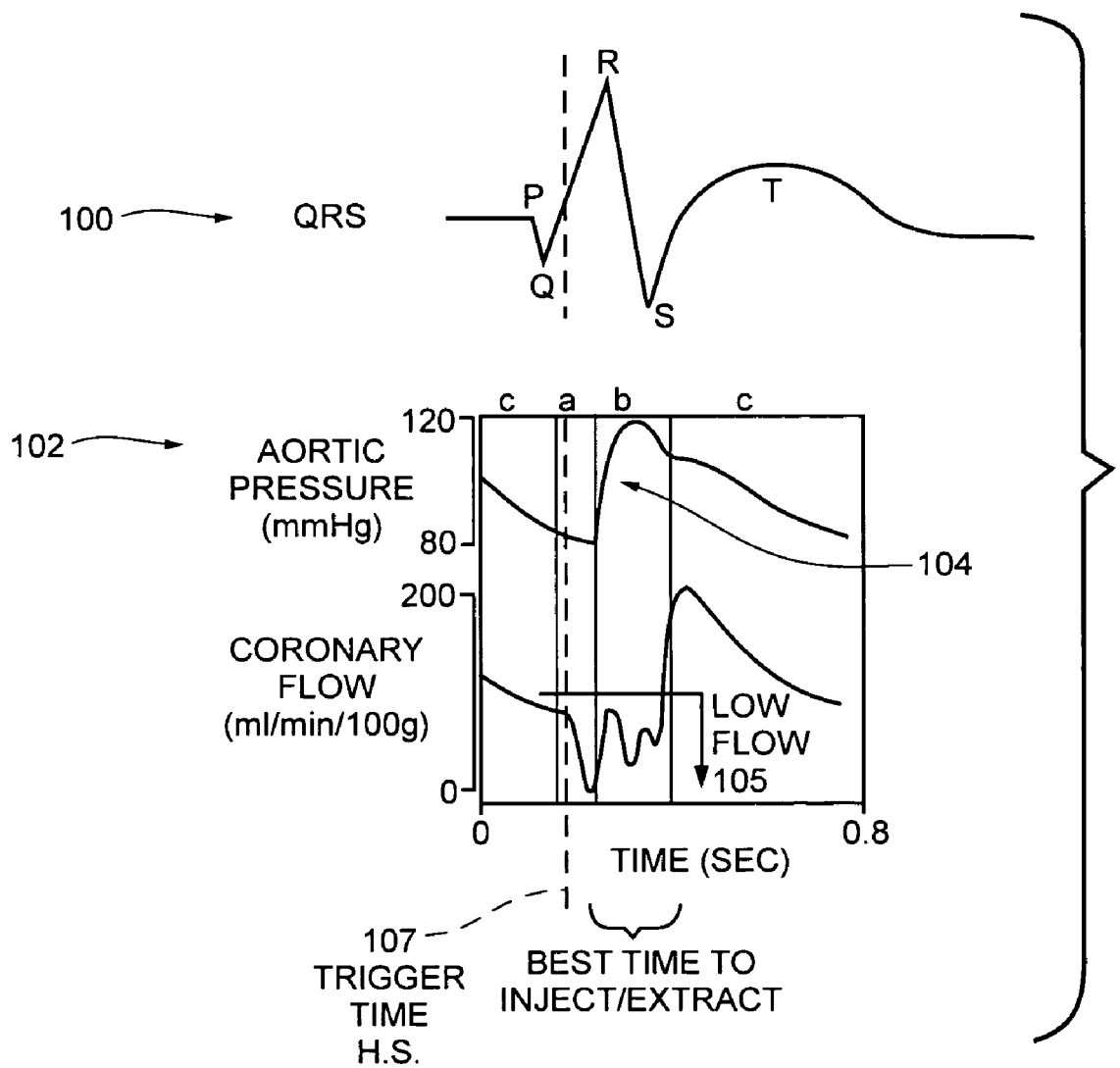
FIG. 12 is a schematic of the invention; and,
FIG. 13 is a schematic of the invention.

FIG. 12 shows a QRS electrocardiograph tracing of the heart over a chart showing the time course of pressure in the aorta and flow in the coronary vessels. The optimal time to inject fluid into the coronary vessel may be when the flow in the vessels is very low 105 due to ventricular contraction. At the isovolumeic, time the aortic pressure is rising very fast 104 and this helps to promote vigorous flow in the guide sheath lumen 7 out of the body.

Figure 11:
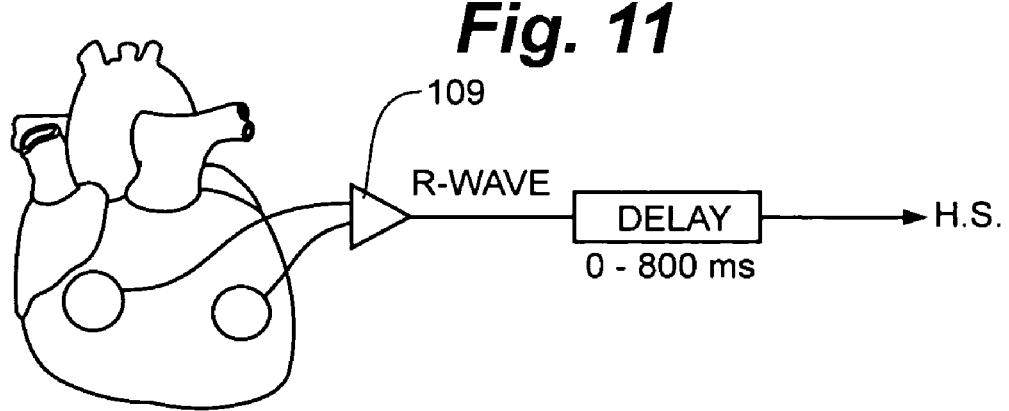
FIG. 11 is a schematic of the invention.

FIG. 11 shows a system to create the trigger time signal depicted as 107 in FIG. 12. Conventional surface electrodes over the heart sense the cardiac depolarization and are amplified in a sense amplifier 109 this signal triggers a delay timer which may delay the activation of the remaining circuits for a few milliseconds. Depending on the overall architecture of the system any one of several approaches to controlling the system may be taken.

Figure 9:
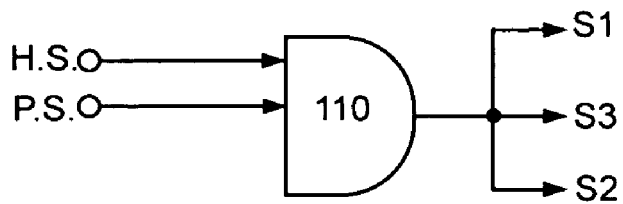
FIG. 9 is a schematic of the invention.

For example FIG. 9 assumes that a catheter structure taught by FIGS. 6 and 7 is set up with for example a conventional injector 30 coupled to the inlet 9 and a vacuum contain attached to the outlet port 40. In this instance, the physician signals his desire to deflate the balloon by activating the physician switch P.S. This is ANDED with the next R0-wave signal processed to give the heart signal H.S. With the and condition satisfied the logic 110 drives the switches S1 which opens the sheath lumen 7 to the collection vessel. Essentially simultaneously, the balloon 20 is deflated by valve S2. At essentially the same time, the injector 30 is turned on by switch S3. Under these conditions, the particles 27 are displaced toward the lumen 7 by the volume of injected fluid at 9. Of course both anntegrade flow and retrograde flow occur with the simple fluid injection but the injected volume is set to exceed the ability of the vascular bed to accept the fluid forcing particulate retrograde into the waiting lumen 7.

Figure 10:
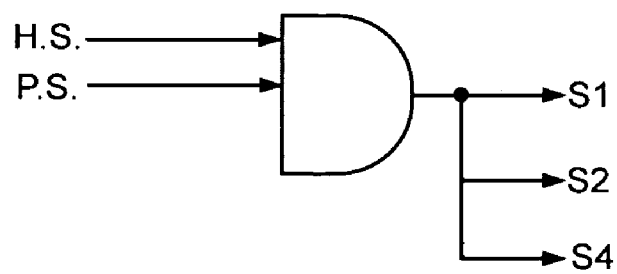
FIG. 10 is a schematic of the invention.

In FIG. 10 a different architecture may be employed for example a manual syringe may be connected as a fluid source for injection 9 and a collection bag 52. In this instance the physician signal to deflate is ANDED with the heart signal H.S. and the deflation switch S2 quickly deflates the balloon 20 while the closure of S4 allows fluid from the syringe to enter the vessel 22 through guidewire lumen in catheter 16. The opening of valve 40 by the closure of switch S1 allows the collected debris and blood and injectate to flow out of the system. Once these processes are started they may terminate within one heartbeat or they may continue over several beats. In general, the closure of the fluid injection process with precedes the closure of the sheath valve 40.

Figure 13:
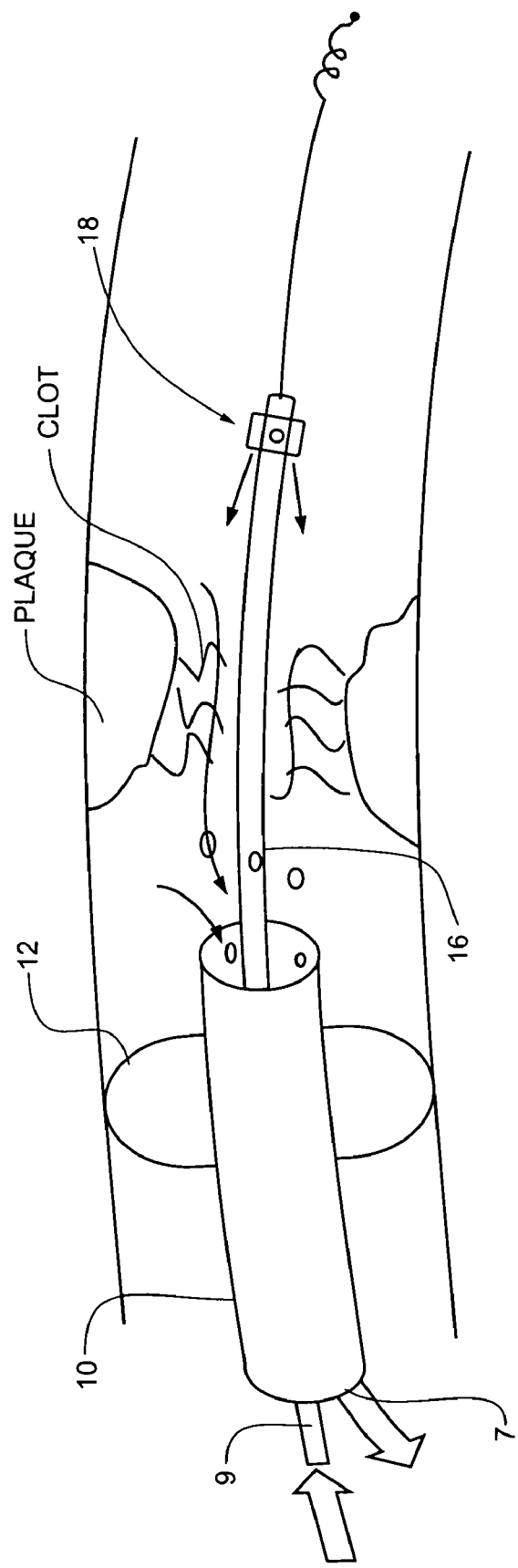

FIG. 13 shows a simplified system for treating acute myocardial infarction. In these cases, the vessel is occluded by a plaque lesion, which is blocked by a clot. By pushing a catheter with a retrograde induction, nozzle 18 on it through the clot the clot is cleared and the clot debris may be collected by the sheath lumen. Again, the occlusion balloon 12 on the sheath 10 is optional. When used it is inflated just before the clot is crossed and is deflated as the nozzle 18 is retracted into the sheath 10. Once again any fluid source and any collection vessel as depicted in FIG. 8 may be used with this embodiment.

It must be recognized that various combinations of injectors and extractors as set forth in FIG. 8 may be arranged to carry out the invention.

Overall System Architecture

FIG. 14 through FIG. 21 show several exemplary basic architectures for the fluidic interventional catheter system. In each figure, the system is shown within a blood vessel 125. In general the system is disclosed in the context of the treatment of coronary vessel disease and the system may be used in coronary arterial vessels of the heart and in saphanous veins harvested and implanted as coronary bypass vessels. The system may also be used in other vessels such as the carotids or other body lumens.

The fluidic interventional catheter 110 shown in FIG. 10 has one extraction section 112 located near the distal tip of the catheter. At the proximal end of the catheter 110 there is a fluid injection port 114 for the injection of primary fluid. The fluid injection port is in fluid communication with the extraction section 112 at the distal tip. In this version of the fluidic catheter there is a guidewire port 116 located at the proximal end of the catheter 110 for using the catheter 110 with a conventional guidewire 118. Although an over-the-wire guidewire port is shown, rapid exchange or single operator exchange versions are contemplated within the scope of claims as well.

Figure 14:
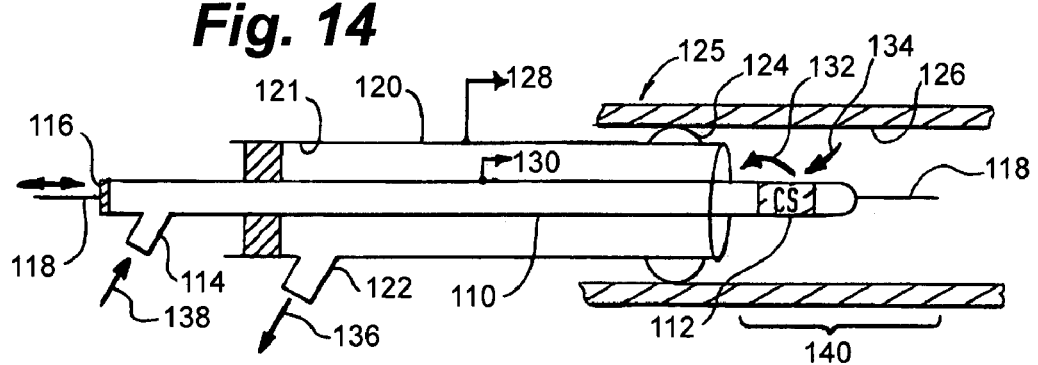
FIG. 14 is a schematic of device architecture.

In FIG. 14 the catheter 110 is shown in an introducer sheath or guide catheter 120. The guide catheter or sheath 120 is shown with a port 122 for extracting entrained fluid at the proximal end of the sheath. An optional balloon structure 124 may be provided to seal the sheath 120 to the vessel lumen 126 or cavity. This balloon 124 is shown adjacent the distal end of the sheath 120. In most embodiments the sheath 120 and the catheter 110 are free to move with respect to each other as indicated by motion arrow 128 and motion arrow 130.

In operation, the extraction section 112 emits a primary fluid flow indicated by fluid arrow 132. Although this fluid will be ejected from all around the periphery of the catheter it is shown as a single flow emerging from one side of the extraction section 112 for clarity. It should be understood that the arrow 132 depicts the primary fluid regardless of jet angle or wall angle and is intended to depict generally the direction of flow and not the particular physics of any particular design. Ambient fluid near the extraction section 112 is entrained according to the wall attachment effect, and this entrained flow is indicated by fluid arrow 134. The combined flow exits the sheath through port 122 as indicated by flow arrow 136.

Thus, primary fluid injected into the catheter (depicted in the figure by fluid arrow 138) emerges from the extraction section 112 (depicted as flow 132) and interacts with ambient fluid (depicted as flow 134) resulting in a combined flow (depicted as flow 136) exiting the sheath at port 122. This convention is used though to depict the injected flow as 132 the entrained flow as 134 or 142 (depending on origin) and the combined flow as 136.

In this simple configuration the extraction section 112 interacts with the body at the treatment zone 140 in the vessel lumen 126. This architecture is useful for use with a standard guidewire 118. If a contrast enhancing fluid is injected into the device under substantial pressure the resulting vigorous jet emerging from the extraction section fills the vessel and reveals the shape of the occlusions in the treatment zone 140. Contrast agent can also be injected though the sheath lumen 121. This architecture is also useful for carotid protection during stenting where the fluidic intervention catheter 110 forces retrograde flow in a vessel during stenting in a companion vessel. Once again the injection of contrast agent permits the confirmation of retrograde flow.

Figure 15:
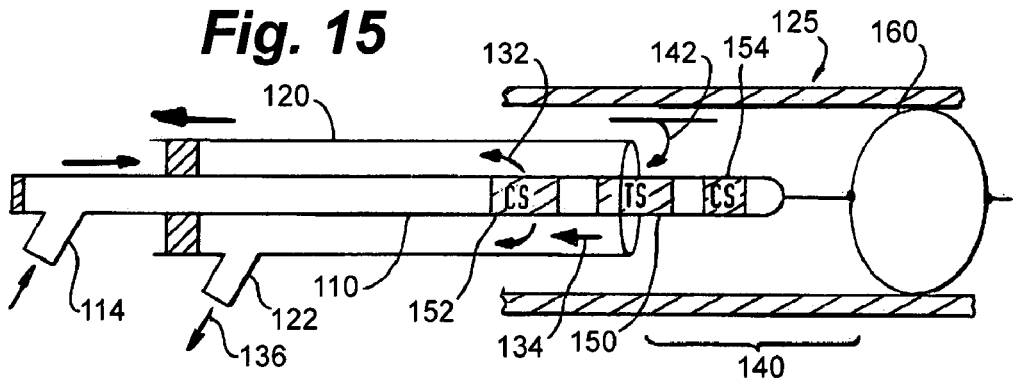
FIG. 15 is a schematic of device architecture.

FIG. 15 is an example of a system architecture which includes a therapy section 150 on the fluidic catheter 110. An extraction section 154 may be placed proximally of the therapy section 150 as illustrated. In the alternative the extraction section may be placed distally as indicated by extraction section 154. Each extraction section may be used alone or with an optional companion extraction section.

This figure serves to illustrate several contemplated embodiments. These embodiments include devices with extraction sections both proximal and distal of a single therapy section as well as devices with a single extraction section proximal of a therapy section and devices with an extraction section proximal of a therapy section. Also illustrated are devices with multiple therapy sections and multiple extraction sections.

As seen in FIG. 15, the extraction section 152 is located within the sheath 120. This extraction section operates as a pump with the retrograde flow 132 inducing a secondary entrained flow 134 which extracts ambient fluid 42 from the treatment zone 140. As indicated in the figure, the extraction section 112 may promote flow of fluid from the retrograde direction as indicated by the direction of flow arrow 142. However, it should be understood that the extraction section could be reversed in direction and used to inject fluid in the antegrade direction as well.

In this particular figure a balloon occlusion device 160 is shown deployed from the guidewire lumen of the device 110. Occlusion devices such as the Medtronic AVE "Guardwire" are available to close off vessels by inflating a balloon. Alternate occlusion devices include filters which may be deployed in the same location. An example of a filter type occlusion device is the "Angiogard" wire is currently undergoing clinical testing.

The term "occlusion device" encompasses both total occlusion devices such as occlusion balloons 160 and filter type occlusion devices 162. In the figures one may substitute one form of occlusion device for the other in most instances with only minor modification of the interventional procedure. If a total occlusion device such as a balloon 160 is used the entrained flow may come from the area of the balloon or it may come from the area between the outside of the sheath 120 and the lumen 126 of the vessel or both locations as indicated by flow arrow 142. One should note that in FIG. 12 there is no balloon sealing the sheath or guide catheter so coronary blood flow is available to be drawn into the lumen of the sheath 120 by the pumping action of the extraction section 152. This incoming flow 142 replaces fluid ejected from the extraction section 152 depicted by flow arrow 132. The two extraction sections 154 and 152 may be operated together or separately.

Figure 16:
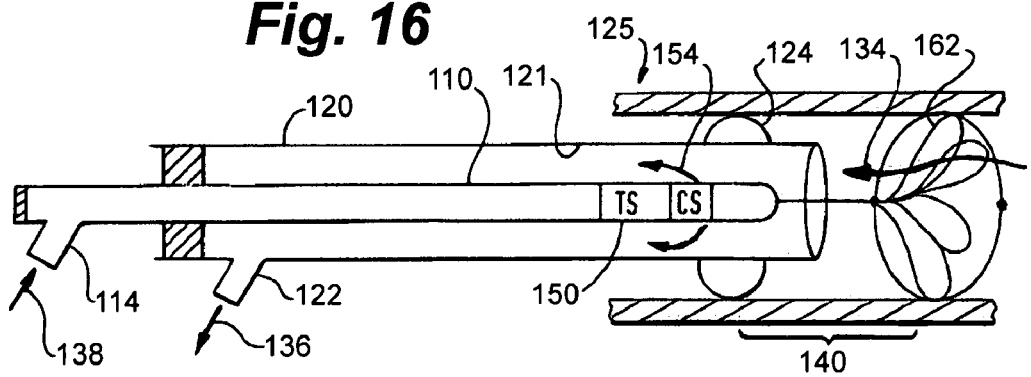
FIG. 16 is a schematic of device architecture.

FIG. 16 shows a fluidic catheter 110 located directly adjacent a therapy section 150. Here the extraction section 154 can be used as a pump for removing debris from a filter type occlusion device 162. In this particular embodiment a balloon 124 on the sheath is inflated to seal off the vessel so that the bulk of the entrained flow 134 is drawn directly from and through the occlusion device shown as a filter 162. In this architecture, the fluidic catheter and its extraction section 154 are used in connection with a treatment section 150 to treat the treatment zone 140 and to remove debris created by that treatment. An example of a treatment section 150 useful in this architecture is an angioplasty balloon or a stent placement balloon. It must also be recognized that the balloon 124 may not be required. This is especially true if the extraction section 154 is located within the sheath 120 and is shrouded by the lumen 121 as shown in the figure.

Figure 17:
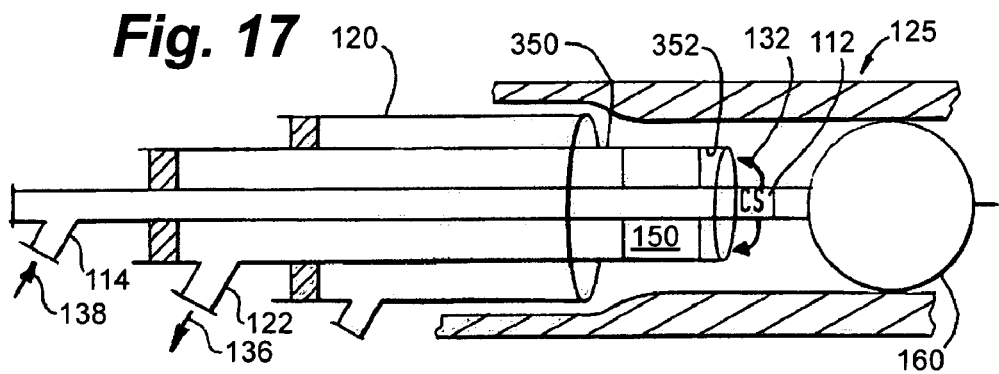
FIG. 17 is a schematic of device architecture.

FIG. 17 shows an alternate architecture where a fluidic catheter 110 is being used to provide hydraulic distal protection in one branch of a bifurcation while a therapy is proceeding in an adjacent vessel. In the figure a balloon 300 is being used in the internal carotid 302 to treat a lesion 304 in a treatment zone 306. An occlusion device 308 is placed distal of the lesion and it blocks the flow of particulates downstream toward the brain. After the balloon 208 is deflated the extraction section 310 will be activated to propel debris toward the open lumen 311 of the sheath 312 located in the common carotid 314. An auxiliary extraction section 318 proximal of the treatment balloon 300 may be used to assist in clearing the vessel.

The sheath 312 may have an optional balloon 124 to seal the common carotid during the intervention. When the balloon is deflated though port 316 the physician will activate both the extraction section 310 carried on the balloon therapy device while activating the extraction section 112 on the device 110 located in the external carotid 320. The primary flow forces the combined flow 136 into the open lumen of the sheath 312. This fluidic jet 132 and associated flow 134 provides a protected zone 324 in the companion vessel 320 which prevents the debris from the treatment zone 306 from entering the external carotid 320. This strategy is especially useful when the balloon 124 is deflated or not present. In this case the blood flow from the common carotid can enter the external carotid until the physician actives the extraction section 112 on the device 110 which then temporally reverses flow in the vessel.

An auxiliary extraction section 322 may be placed in the open lumen 311 of the sheath 312 to eject debris from the body.

Figure 18:
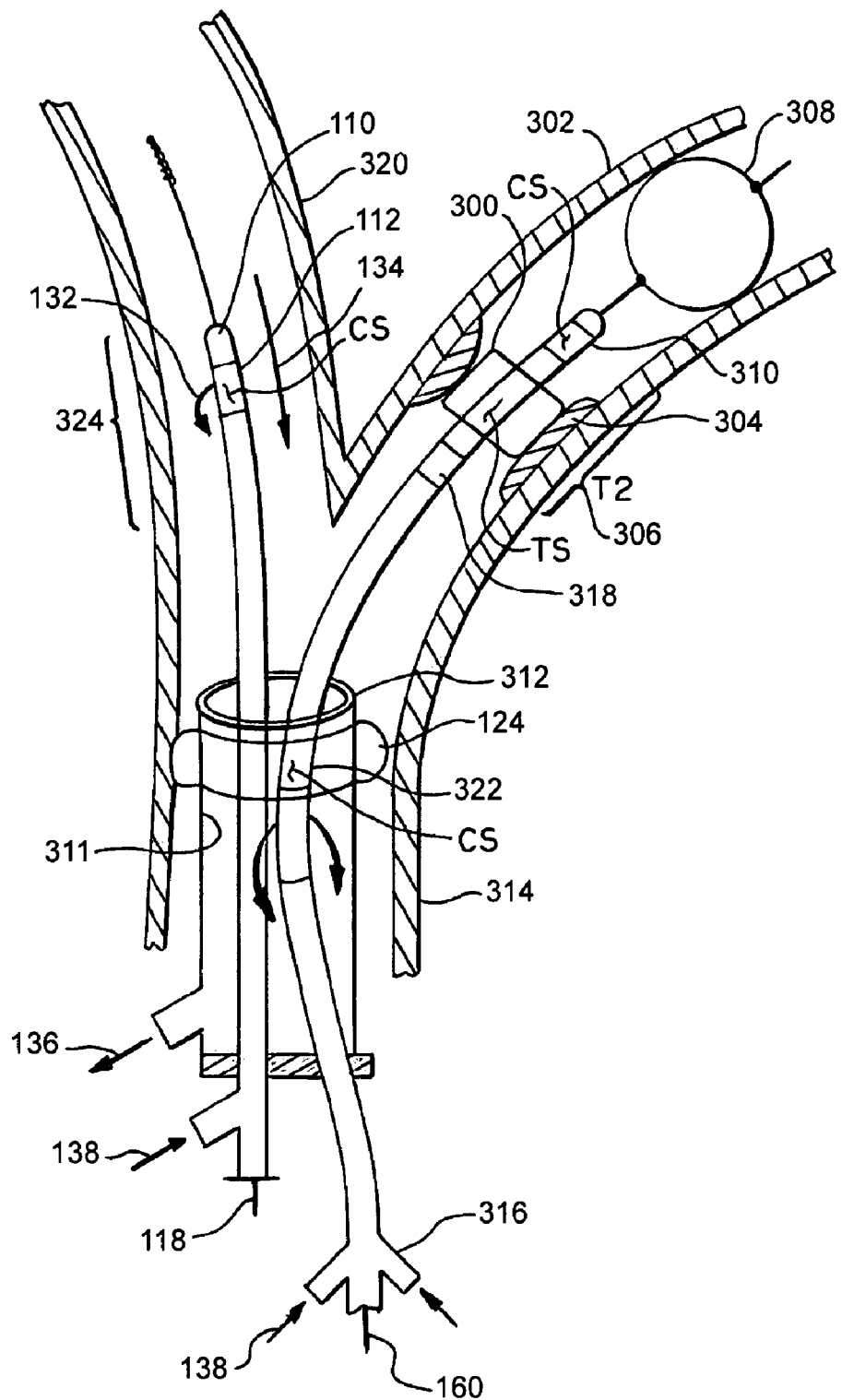
FIG. 18 is a schematic of device architecture.

FIG. 18 shows an extraction section 112 combined with a distal protection device of the balloon type. In this embodiment an occlusion filter may be substituted for the balloon. In FIG. 18 the therapy section 150 is on a separate catheter 350 that incorporates an extraction lumen 352. In use, after the therapeutic intervention the therapy catheter 350 is advanced toward the occlusion balloon 160 and the majority of the entrained flow will exit the therapy catheter as depicted by flow 136. This flow is propelled by the extraction section 112 operating in the vessel and then operating in the lumen 352.

In summary, the extraction section may be used alone or combined with a therapy device. More specifically the extraction section may reside on an angioplasty catheter, or a distal protection catheter or it may be used alone in the vessel or catheter lumen.

The Extraction Section Geometry

The extraction section 112 may take any one of several forms. In the figures the extraction sections may take the form of FIG. 19 or FIG. 20. The FIG. 21 embodiments would require complimentary changes to be used in the architectures depicted in FIGS. 10-15.

In general all embodiments rely on the wall attachment effect which is sometimes called the Coanda effect. Wall attachment occurs when the injected fluid emerges near a wall or barrier and begins to entrain ambient fluid. The entrainment process causes the emerging jet to be pushed against the wall. Once the emerging jet is attached to the wall it will follow the wall contour for a long distance. The geometry of the extraction section is quite flexible and numerous geometric combinations will exhibit a useful wall attachment effect.

To define the extraction section it is useful to first define certain axises and angles. First, there is a geometric axis for the fluid as it emerges from the fluid supply lumen called "jet axis". This axis is defined as the direction that the jet squirts when the device is operated in air. This may be tested by suspending the device in air and injecting distilled water into the device.

The long length of the catheter body will carry the fluid supply lumen and the fluid supply lumen has a "lumen axis". The body of the catheter has a "body axis". In most instances the body axis is parallel to the supply "lumen axis".

The angle between the body axis and the jet axis is the "jet angle" measured from the body axis as seen in figures and labeled JA in the figures. This JA angle may vary from about 90 degrees where the jet is directed directly radially from the body through 180 degrees where the geometric axis points in the proximal or retrograde direction. Beyond 180 degrees the nozzle becomes "internal" as described in FIG. 21.

The wall or barrier is located proximate the jet and it forms an angle with respect to the geometric jet axis or JA. This wall angle WA can vary from about 0 degrees where the jet axis is both tangent and parallel to the wall to about 45 degrees or more. As the wall angle WA increases from 0 to 45 degrees or more it take more time for the jet to attach to the wall after the jet emerges. However the jet, once attached is stable and the turbulence and vorticity is very large. As the jet angle decreases from about 180 degrees to about 90 degrees the effective diameter of the entrained flow increases and the turbulence increases.

Details of construction may vary widely and are known to those of ordinary skill in this art. When the flow rates are low, multiple individual lumens may be use to supply fluid to a distal cap area. A slit or gap may be provided to provide an exit for the fluid and it may directed at any convenient "jet angle". The attachment wall or surface may be formed by a separate bead or nubbin placed near the slit or gap. A single annular slit or gap is preferred but a number of individual jets may be used as well. In general the wall angle must be reduced to get good attachment with individual jets. If the jet angle is about 135 degrees the catheter body itself may form the attachment wall. The problem with individual jets is that the "edges" of the jets allow for ventilation of the underside of the jet.

Figure 21:
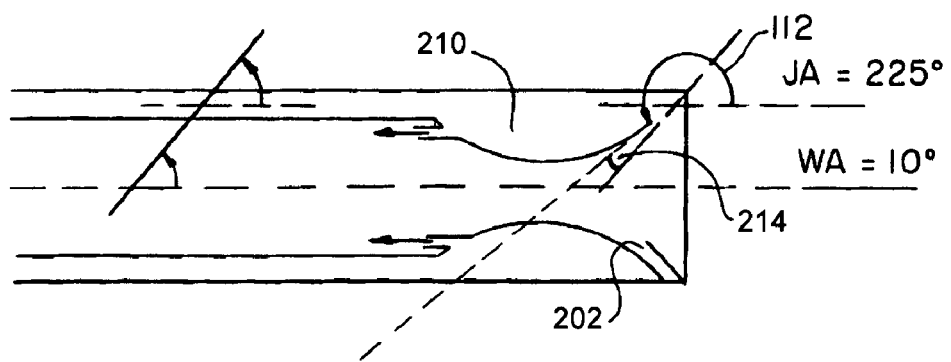
FIG. 21 is a schematic of the extraction section geometry.

When the jet angle is extended beyond 180 to approximately 225 degrees the wall attachment nozzle goes from "external" as seen in FIGS. 6 and 7 to "internal" as seen in FIG. 21.

Experimentation has shown that a small enlargement of the supply lumen adjacent to the fluid supply gap improves the stability of the attached jet. This navicular fossa 210 region seems to promote stable attachment of the jet to the wall. A suitable location for this volume is identified with ref numeral 210 in each of FIGS. 6 7 and 8.

Figure 19:
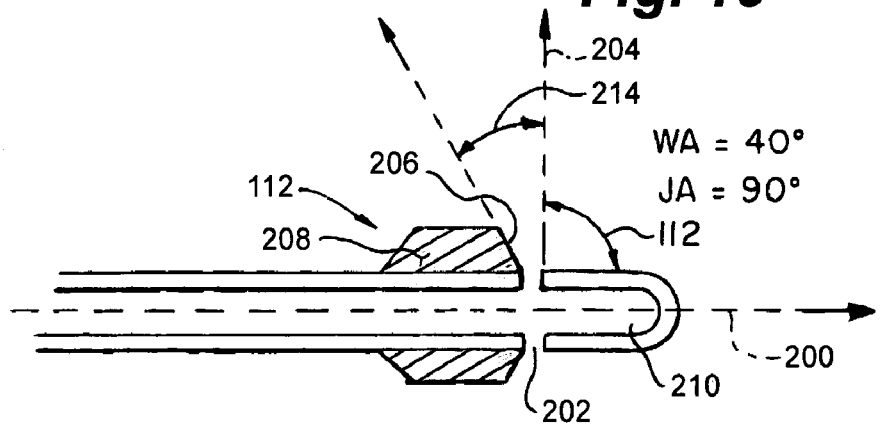
FIG. 19 is a schematic of the extraction section geometry.
Figure 20:
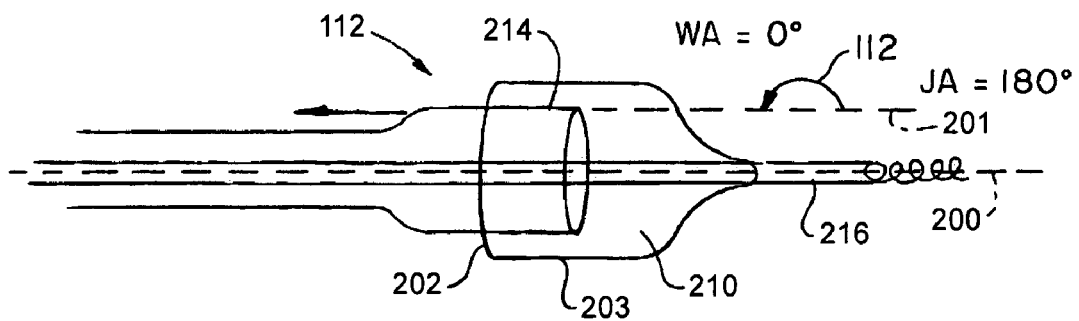
FIG. 20 is a schematic of the extraction section geometry.

FIG. 19 FIG. 20 and FIG. 21 should be considered together as they show the development of variations of the wall attachment jet geometry for the extraction section of the catheter.

In FIG. 19 the catheter body and the single lumen share the same axis 200. A slit or series of slits surround the catheter body forming exit jet apertures typified by jet aperture 202. When operated in air the fluid emerging from the jet apertures flows a path indicated by arrow 204. This jet direction is used to defined the "jet angle" 212 on the figure, It is measured counterclockwise from the catheter axis 200 and is approximately 90 degrees in FIG. 19. The conical wall 206 is placed near the jet aperture 202 and the angle tangent to the wall measured toward the jet direction or JA is the "wall angle" or WA 214. In this figure the wall angle is about 40 degrees. In operation, the fluid starts out in the jet direction and attaches to and follows the contour of the nubbin 108. FIG. 19 is an example of an extraction section 112 with a jet angle of about 90 degrees and a wall angle of about 40 degrees.

In FIG. 20 the catheter body and the fluid supply lumen share the same direction 101. In this configuration the jet angle 212 is increased to 180 degrees and it points directly rearward in the sense of the figure. In this particular design the guidewire lumen 216 tube provides a convenient location to bond the over-tube 203 which forms the gap or slit 202. This nozzle represents an extraction section 112 with a jet angle of 180 degrees and a wall angle of 0 degrees.

In FIG. 21 the nozzle has been turned inside out and forms an internal rather than external nozzle. In this geometry the jet angle has been increased to 225 degrees and now points inward. The wall angle is about 10 degrees. A set of auxiliary jets typified by jet 218 can be provided as well. It too achieves wall attachment on the internal surfaces of the device.

Exemplary Methods of Use

FIG. 22 depicts a method of use for a simple fluidic interventional catheter 210 used in conjunction with a balloon angioplasty procedure. In this particular example a balloon 260 occlusion device is first advanced into the vessel past the treatment zone 240. Next, the balloon catheter 360 is inflated to treat the lesion in the treatment zone by expanding the balloon 280 into the lesion.

Next, the treatment catheter 260 is removed and a fluidic catheter 110 is guided to the treatment zone 140 along the occlusion wire 362 as depicted in FIG. 23. Primary fluid 132 which may be radiopaque or normal saline is injected in to the extraction section 112 and the entrained flow 134 is propelled out of the lumen of the sheath 120. The sheath may be fixed and the catheter moved toward the balloon 160 as indicated by arrow 130. In the alternative the sheath may be advanced toward the balloon 160 as indicated by arrow 128. It is also desirable in some instances to advance both the sheath 120 and the device 110 simultaneously or sequentially. The balloon 160 may be deflated preferably after the primary flow 132 is turned on. By deflating the balloon 160 after the primary flow is injected particulate typified by particle 144 at the periphery of the balloon will be entrained into the sheath 120 which is desirable.

FIG. 24 depicts a method of use for a simple fluidic interventional catheter 110 used in conjunction with a conventional balloon angioplasty procedure. In this particular example a filter 162 type distal occlusion device is placed in the vessel lumen. The occlusion device 162 is first advanced into the vessel past the treatment zone 140 and deployed to collect debris typified by particle 144.

Next, the balloon catheter 360 is inflated to treat the lesion in the treatment zone 140. The balloon 380 inflates and opens the vessel.

In FIG. 12 the treatment catheter 360 is removed and a fluidic catheter 110 is guided to the treatment zone along the occlusion wire 262. Primary fluid 132 which may be radiopaque or normal saline is injected by the extraction section 112 on the device 110 and the entrained flow is propelled out of the lumen of the sheath 120. The sheath may be fixed and the catheter moved toward the balloon 160. In the alternative the sheath may be advanced toward the filter 162. It is also desirable in some instances to advance both the sheath 120 and the device 110 simultaneously or sequentially. The filter 162 allows blood and debris to be pumped "backwards" into the sheath as indicated by flow 270.

In general filter type devices are useful but they can clog with too much debris which makes removal problematic. In this system the catheter 110 can empty the filter 162 and clear debris 144 before the filter device 162 is removed.

FIG. 26 depicts a method of use for a combined therapy and fluidic interventional catheter 390 used in conjunction with a balloon angioplasty procedure. In this particular example a balloon 160 type distal occlusion device is placed in the vessel lumen. The occlusion device 160 is first advanced into the vessel past the treatment zone 140 and deployed to collect debris released by the procedure.

Next, the combined fluidic and balloon catheter 390 is inflated to treat the lesion in the treatment zone 140. The balloon 380 inflates and opens the vessel.

Next, the extraction section 112 which is carried on the catheter and placed distal of the balloon 380 is activated while the balloon is deflated. It is preferable to activate the extraction section 112 after the catheter is advance toward the occlusion device as indicated by arrow 130. In this intervention the balloon 124 on the sheath 120 is inflated at least during the debris recovery process.

Alternatively, the balloon 380 may be deflated and the device 390 reciprocated several times up and down the wire 362 to clear debris from the treatment zone.

FIG. 28 depicts a method of use for a combined therapy and fluidic interventional catheter 392 used in conjunction with a balloon angioplasty procedure. In this particular example a balloon 160 type distal occlusion device is placed in the vessel lumen. The occlusion device 160 is first advanced into the vessel past the treatment zone 140 and deployed to collect debris released by the procedure.

Next, the combined fluidic and balloon catheter 392 is inflated to treat the lesion in the treatment zone 140. The balloon 380 inflates and opens the vessel.

Next, the extraction section 112 which is carried on the catheter and placed proximal of the balloon 380 is activated while the balloon is deflated. It is preferable to activate the extraction section 112 after the catheter is advance toward the occlusion device. It may also be used while moving away from the occlusion balloon. as indicated by arrow 131. In this intervention the balloon 124 on the sheath 120 is inflated at least during the debris recovery process.

It should be noted that the deflation of the occlusion balloon 160 will result in retrograde flow as indicated by arrow 400. When the extraction section 112 is operating the primary flow 132 entrains the blood 300 and forces the entire flow 136 into the sheath 120.

FIG. 30 depicts a combination catheter 420 with a balloon treatment section having balloon 380 and relatively long proximal "snout" with an extraction section 112 located near its tip. In use, the conventional guidewire 118 is used to traverse the lesion in the treatment zone 140 and the combination catheter is moved into position to treat the lesion.

FIG. 31 shows the combination catheter 420 in position with the balloon 380 inflated to remodel the plaque in the lesion. This process liberates debris typified by particle 144. Since the vessel is occluded by the sheath balloon 124 and by closing off the central lumen of the sheath 120 the particles and other debris will not move very far downstream.

Figure 32:
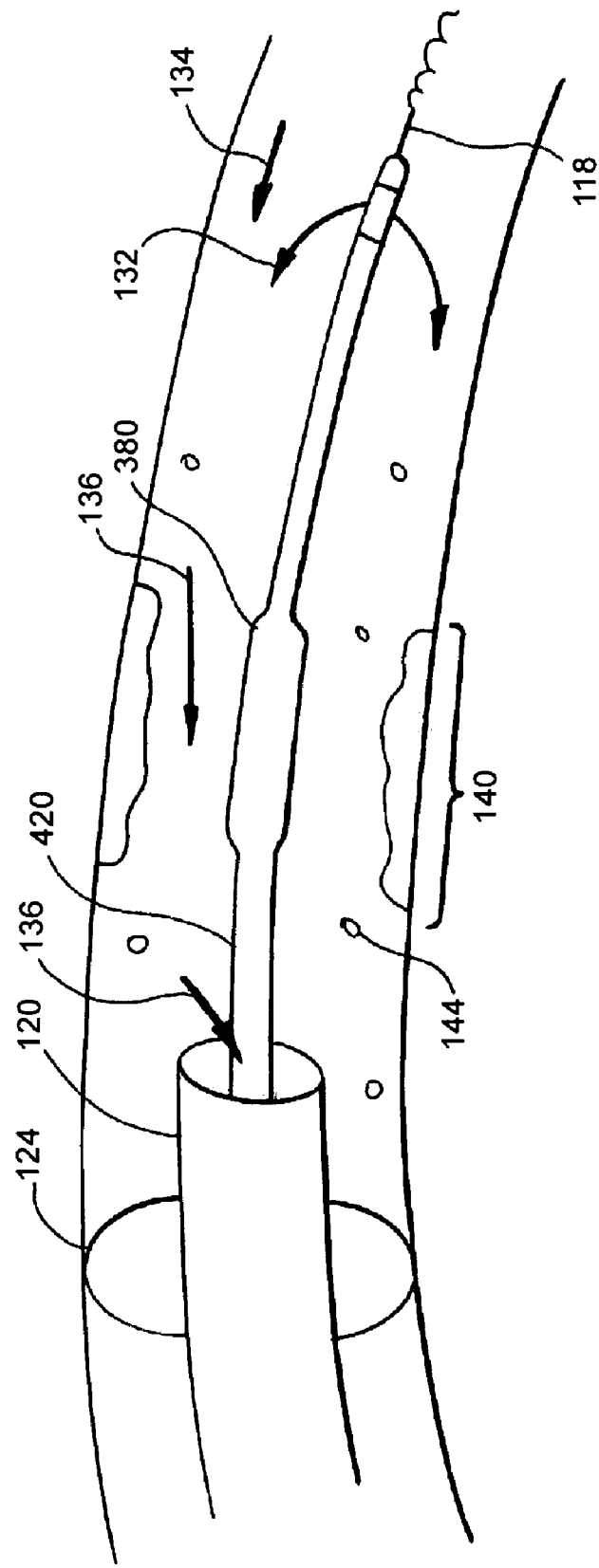

FIG. 32 shows the balloon 380 being deflated as the primary fluid 132 is injected. The induced retrograde flow 136 sweeps the loose particulate into the open lumen of the sheath 120 providing a completely hydraulic form of distal protection. In use the catheter 420 can be withdrawn into the sheath to completely remove particulate liberated by the angioplasty process.

CLAIM LANGUAGE ANTECEDENTS

A method for extracting debris from a vessel having a lesion comprising the steps of:
 placing a therapy catheter in contact with a lesion;
 inflating the therapy balloon to treat the lesion producing debris;
 injecting fluid into a extraction section creating a pressure gradient across the therapy balloon while it is inflated;
 deflating the therapy balloon while injecting fluid to promote a retrograde flow across the surface of the therapy balloon entraining, capturing and moving debris in the retrograde direction.
The method set forth above further including the step of extracting said debris from a location proximal of said extraction section with a tube.
The method set forth above further comprising an initial step of traversing a treatable lesion with an occlusion device and deploying the occlusion device distal of said therapy balloon.
The method set forth above wherein said distal occlusion device is a filter.
The method set forth above wherein said distal occlusion device is an inflatable balloon.

What is claimed is:

1. A method of removing debris from a treatment site comprising the steps of:
 inflating a therapy balloon to provide a therapy and thereby occluding a vessel and making debris;
 injecting fluid distal of said balloon when said balloon is deflated at a rate and at a time in the cardiac cycle corresponding to the R-wave component of the QRS complex in the electrographic waveform to displace debris into a guide sheath lumen placed proximal of the therapy balloon;
 synchronizing the injection of fluid with the electrographic R-wave of the patient so as to inject at a time of low flow in the coronary arteries; and
 removing debris and fluid from said guide sheath as fluid is injected.

2. The method of claim 1 for removing debris from a treatment site comprising the additional steps of:
 at least partial occluding a vessel near a treatment site by inflating an occlusions balloon located on a guide sheath of the type having an open lumen, near the therapy site;
 injecting fluid into the therapy site at a location distal of the therapy site during the intervention at a rate and quantity sufficient to displace the debris into said guide sheath lumen.

3. The method of claim 2 wherein said injecting step is preceded by a therapeutic intervention at a site proximal of said injection site.

* * * * *